(12) United States Patent
Alazmi

(10) Patent No.: US 10,507,129 B2
(45) Date of Patent: Dec. 17, 2019

(54) PELVIC FRACTURE SPLINT

(71) Applicant: Mohammed Saad Farhan Alazmi, Safat (KW)

(72) Inventor: Mohammed Saad Farhan Alazmi, Safat (KW)

( * ) Notice: Subject to any disclaimer, the term of this patent is extended or adjusted under 35 U.S.C. 154(b) by 0 days.

(21) Appl. No.: 16/351,464

(22) Filed: Mar. 12, 2019

(65) Prior Publication Data

US 2019/0274860 A1 Sep. 12, 2019

Related U.S. Application Data

(60) Provisional application No. 62/641,844, filed on Mar. 12, 2018.

(51) Int. Cl.
*A61F 5/24* (2006.01)
*A61F 5/01* (2006.01)

(52) U.S. Cl.
CPC .................... *A61F 5/0193* (2013.01)

(58) Field of Classification Search
CPC ........ A61F 5/0193; A61F 5/026; A61F 5/028; A61F 5/0102; A61F 5/0104; A61F 5/24; A61F 5/26; A61F 5/28; A61F 5/37
USPC ........... 602/67; 128/98.1, 99.1, 102.1
See application file for complete search history.

(56) References Cited

U.S. PATENT DOCUMENTS

| | | | |
|---|---|---|---|
| 4,577,622 A | 3/1986 | Jennings | |
| 4,884,562 A * | 12/1989 | Stone | A61F 5/028 602/19 |
| 5,928,175 A | 7/1999 | Tanaka | |
| 6,503,217 B1 | 1/2003 | Gibbs et al. | |
| 2006/0135898 A1 | 6/2006 | Richardson | |
| 2006/0282032 A1* | 12/2006 | Smith | A61F 5/026 602/19 |
| 2015/0359541 A1* | 12/2015 | Ross | A61H 9/0078 606/203 |
| 2016/0015550 A1 | 1/2016 | Evans et al. | |

OTHER PUBLICATIONS

"Bellyband Groin Bands" Cabea. https://babybellyband.com/product/compression-therapy-groin-bands/.
"FLA Soft Form Hernia Support Belt" Ames walker. https://www.ameswalker.com/products/fla-soft-form-hernia-support-belt.

* cited by examiner

*Primary Examiner* — Anna K Kinsaul
*Assistant Examiner* — Camtu T Nguyen
(74) *Attorney, Agent, or Firm* — Richard C. Litman; Nath, Goldberg & Meyer

(57) ABSTRACT

The pelvic fracture splint includes a first portion having a first end and an opposing second end and a second portion having an opening defined therein, the second portion extending downward from the first portion of the pelvic fracture splint substantially at the mid-section of the first portion. The pelvic fracture splint also includes a plurality of strips (preferably three strips) selectively fastening the opposing ends of the first portion and the second portion of the pelvic fracture splint to secure the pelvic fracture splint around the person's waist or hips and groin. The first portion includes a plurality of splints (rigid supports, preferably six in number) vertically positioned along the first portion at spaced apart positions. The opening in the second portion of the pelvic fracture splint may have a triangular shape to avoid placing any unnecessary pressure on the person's genitals.

7 Claims, 1 Drawing Sheet

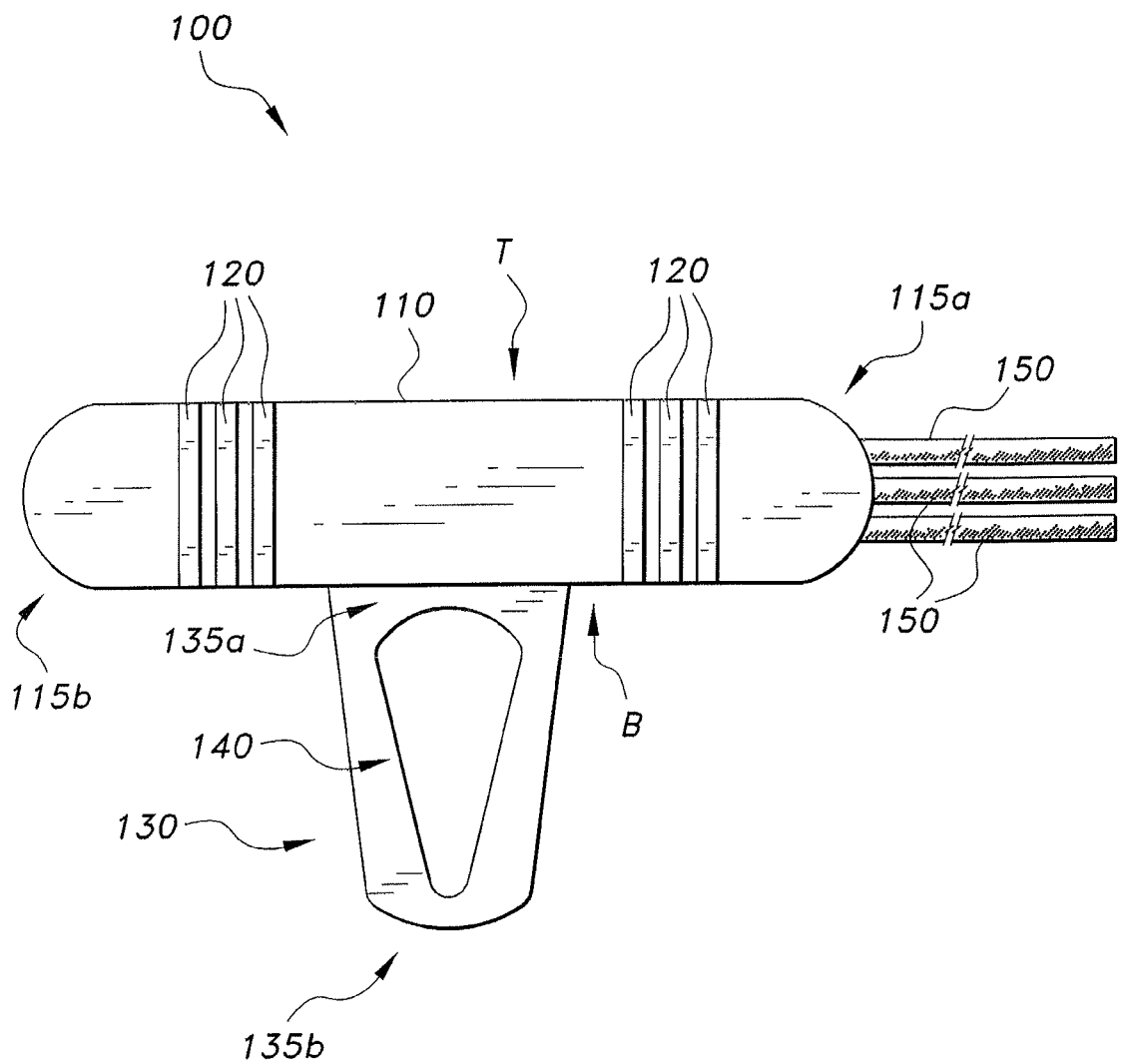

PELVIC FRACTURE SPLINT

CROSS-REFERENCE TO RELATED APPLICATION

This application claims the benefit of U.S. Provisional Patent Application Ser. No. 62/641,844, filed Mar. 12, 2018.

BACKGROUND OF THE INVENTION

1. Field

The present disclosure relates to medical devices, and particularly to a pelvic fracture splint configured for supporting a bone fracture of the pelvis.

2. Description of the Related Art

The human pelvis comprises three pelvic bones that combine to form a strong anatomic ring. As such, a pelvic fracture may disrupt the integrity and stability of the pelvic ring and lead to significant pelvic bleeding, since the arteries and major veins passing through the pelvic area may easily be pinched, torn, or lacerated by the fractured bones. Typically, a splint is used to stabilize the pelvis after a pelvic fracture. While pelvic splints come in a variety of sizes, shapes, and structures, they generally share the same purpose of immobilizing a person's pelvic region to prevent further damage, secondary injury, or undue pain due to the unrestrained movement thereof.

Devices commonly used to immobilize a patient to prevent further injury include rigid splints, inflatable splints, and vacuum immobilization splints. These devices, however, have various drawbacks, including the inability to conform to features of individual patients. Rigid splints are typically difficult to store, cumbersome to use, and may not completely and effectively immobilize the injured part of the body due to poor fit, leading to the possibility of exacerbation of the injury or secondary trauma. Further, inflatable splints can expand toward the injured extremity and impart pressure thereon, which, in turn, can restrict blood flow.

Thus, a pelvic fracture splint solving the aforementioned problems is desired.

SUMMARY

The pelvic fracture splint includes a first portion having a first end and an opposing second end, and a second portion having an opening, the second portion extending downward from the first portion of the pelvic fracture splint, preferably at the mid-section of the first portion. The pelvic fracture splint also includes a plurality of strips (preferably three strips) connecting the opposing ends of the first portion and the second portion to secure the pelvic fracture splint around the person's waist. The first portion includes a plurality of rigid supports (preferably six supports) vertically positioned along the first portion at spaced positions. The opening in the second portion of the pelvic fracture splint may have a triangular shape in order to avoid any unnecessary pressure on the person's genitals.

These and other features of the present disclosure will become readily apparent upon further review of the following specification and drawings.

BRIEF DESCRIPTION OF THE DRAWINGS

The sole drawing FIGURE is a front view of a pelvic fracture splint.

DETAILED DESCRIPTION OF THE PREFERRED EMBODIMENTS

Referring to the drawing, a pelvic fracture splint 100 configured for supporting a bone fracture of the pelvis is generally illustrated. The pelvic fracture splint 100 includes a first portion 110 having a plurality of rigid splints 120 (preferably six splints 120) vertically positioned along the first portion 110 at spaced apart positions, a second portion 130 having an opening 140 defined therein, the second portion 130 extending downward from the first portion 110 of the pelvic fracture splint 100, and a plurality of strips 150 (preferably three strips 150) selectively connecting the first portion 110 and the second portion 130 of the pelvic fracture splint 100 to secure the pelvic fracture splint 100 around the person's waist and pelvic region.

The first portion 110, or hip support portion, of the pelvic fracture splint 100 is elongated has a first end 115*a* and an opposing second end 115*b*, and is configured for wrapping around the person's waist or hips to provide support for the hips and the buttocks. The fastener strips 150 are shown in the drawing extending from the first end 115*a* of the first portion 110. The first portion 110 can be formed from any suitable type of flexible material, such as plastic, and can have any suitable length in order to fit people having different waist sizes, such as small, medium, and large. Further, each of the splints 120 positioned along the first portion 110 of the pelvic fracture splint 100 can be formed from any suitable material, such as wood or plastic. Each splint 120 extends vertically from the top side T to the bottom side B of the first portion 110 of the pelvic fracture splint 100, such that when the first portion 110 of the fracture splint 100 is wrapped around the person's waist, the splints 120 are positioned along the right side and the left side of the person's pelvis.

The second portion 130, or groin support portion, of the pelvic fracture splint 100 includes a first end 135*a* attached to the bottom side B of the first portion 110, such as at the mid-section of the first portion 110, and an opposing second end 135*b* extending away from the first portion 110. The second portion 130 can be formed from any suitable type of flexible material, such as plastic. The second portion 130 of the pelvic fracture splint 100 is adapted for being wrapped underneath the person's groin region and attached to the ends 115*a*, 115*b* of the first portion 110 by the plurality of strips 150, such that the person's genitals (in the case of a male patient) can be inserted through the opening 140 of the second portion 130 of the pelvic fracture splint 100. The opening 140 in the second portion 130 of the pelvic fracture splint 100 can have any suitable shape, such as a triangular shape to avoid any unnecessary pressure on the person's genitals.

The plurality of strips 150 and second end 135*b* of the second portion 130 may be connected by adhesive strips or fastener strips (e.g., Velcro®), that can fasten the second end 135*b* (i.e., the free end) of the second portion 130 to the ends 115*a*, 115*b* of the first portion 110. The strips 150 may, e.g., be the hook portion of a hook and loop fastener attached to the first end 115*a* by adhesive, glue, ultrasonic welding, or other means, and the second end 115*b* of the first portion 110 and the second end 135*b* of the second portion may be made from a loosely woven fabric forming loops that the strips 150 may secure to firmly enough to keep the first portion 110 and second portion 130 of the splint 100 in place for supporting the hip area and the groin area, or the second ends 115b and 135b may have mating strips or patches of hook and loop fastening material attached or bonded thereto.

By way of operation, the person first inserts his genitals into the opening 140 of the second portion 130 of the pelvic fracture splint 100, such that the person's genitals can serve as an anchor for the pelvic fracture splint 100. Once the pelvic fracture splint 100 is properly positioned, the second end 135b of the second portion 130 of the pelvic fracture splint 100 is then pulled underneath the groin so that the second end 135b of the second portion 130 can be attached to the opposing ends 115a, 115b of the first portion 110 of the pelvic fracture splint 100 through the plurality of strips 150. Each of the strips 150 can be adjusted to ensure a tight fit around the person's waist, such that each splint 120 is positioned along the patient's sides. It is to be noted that the splints 120 are preferably equidistantly spaced so that the splints 120 can effectively immobilize the injured part of the pelvic region.

Once the first portion 110 of the pelvic fracture splint 100 has been adjusted to fit around the person's waist, the person can adjust his genitals within the opening 140 in the second portion 130 of the pelvic fracture splint 100 to avoid any unnecessary pressure on the genitals. He can wear the pelvic fracture splint 100 so long as necessary to stabilize and cure the pelvic fracture.

It is to be understood that the pelvic fracture splint is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A pelvic fracture splint, consisting of:
   an elongated first portion having a first end and an opposing second end and defining a length, the first elongated portion being adapted for supporting hips of a person suffering a pelvic fracture;
   a plurality of rigid splints oriented orthogonal to the length of the first elongated portion and spaced apart along the first elongated portion, the plurality of rigid splints includes a first group of multiple rigid splints and a second group of multiple rigid splints, wherein the first and second groups of multiple rigid splints are spaced apart along the length of the first elongated portion and adapted for supporting opposite sides of the pelvis;
   a second portion consisting of an opening defined therein, the second portion being made from a flexible, non-elastic material, the second portion having a first end attached to the first elongated portion and extending downward from the first elongated portion and having a second end, wherein the second end is free-standing and adapted for wrapping about and supporting a groin area of the person suffering the pelvic fracture, further wherein the second end is attached to the first elongated portion; and
   a plurality of fastener strips extending from the first end of the first elongated portion, each of the plurality of fastener strips being fastenable to the second end of the first elongated portion and the second end of the second portion to secure the first elongated portion around the hips and the second portion under the groin area of the person suffering a pelvic fracture.

2. The pelvic fracture splint of claim 1, wherein the second portion is positioned halfway between the first and second ends of the first portion.

3. The pelvic fracture splint of claim 1, wherein a first distance between the first end of the first elongated portion and the first group of multiple rigid splints is equal to a second distance between the second end of the first elongated portion and the second group of multiple rigid splints.

4. The pelvic fracture splint of claim 1, wherein each of the first group and second groups of multiple rigid splints includes three equally spaced splints aligned in parallel.

5. The pelvic fracture splint of claim 1, wherein the opening in the second portion tapers inwards as the opening extends downward from the first elongated portion.

6. The pelvic fracture splint of claim 1, wherein the second end of the second portion includes a fastener.

7. The pelvic fracture splint of claim 1, wherein a middle portion of at least one of the fastener strips includes a fastener.

* * * * *